(12) United States Patent
Gan et al.

(10) Patent No.: US 9,883,917 B2
(45) Date of Patent: Feb. 6, 2018

(54) SKIN DILATOR

(71) Applicant: SHANGHAI NINTH PEOPLE'S HOSPITAL AFFILIATED, SHANGHAI JIAOTONG UNIVERSITY SCHOOL OF MEDICINE, Shanghai (CN)

(72) Inventors: Yaokai Gan, Shanghai (CN); Kerong Dai, Shanghai (CN); Qingfeng Li, Shanghai (CN)

(73) Assignee: SHANGHAI NINTH PEOPLE'S HOSPITAL AFFILIATED, SHANGHAI JIAOTONG, UNIVERSITY SCHOOL OF MEDICINE, Shanghai (CN)

( * ) Notice: Subject to any disclaimer, the term of this patent is extended or adjusted under 35 U.S.C. 154(b) by 182 days.

(21) Appl. No.: 15/031,731

(22) PCT Filed: Mar. 13, 2014

(86) PCT No.: PCT/CN2014/073399
§ 371 (c)(1),
(2) Date: Apr. 23, 2016

(87) PCT Pub. No.: WO2015/062196
PCT Pub. Date: May 7, 2015

(65) Prior Publication Data
US 2016/0242864 A1 Aug. 25, 2016

(30) Foreign Application Priority Data
Nov. 4, 2013 (CN) .......................... 2013 1 0539646

(51) Int. Cl.
*A61M 29/00* (2006.01)
*A61B 90/00* (2016.01)
*A61M 29/02* (2006.01)

(52) U.S. Cl.
CPC ............. *A61B 90/02* (2016.02); *A61M 29/02* (2013.01); *A61B 2217/007* (2013.01); *A61M 2210/04* (2013.01)

(58) Field of Classification Search
CPC .............. A61M 29/02; A61M 2210/04; A61B 2217/007
See application file for complete search history.

(56) References Cited

U.S. PATENT DOCUMENTS 4,685,447 A * 8/1987 Iversen ................. A61F 2/0059
128/899
4,800,901 A * 1/1989 Rosenberg ............. A61B 90/02
128/899

(Continued)

*Primary Examiner* — Son Dang
(74) *Attorney, Agent, or Firm* — CBM Patent Consulting, LLC

(57) ABSTRACT

Disclosed is a skin dilator, comprising an expander (11), a pipe network provided on the skin-side surface wall (111) of the expander (11) composed of longitudinal tube (22) and horizontal tube (21) having a reticular structure and communicating with each other, and a guide tube (24) communicating with the pipe network. The skin dilator further comprises several burrs (25) distributed on the skin-side surface wall (111) of the expander (11), and several small apertures (23) communicating the inner cavity of the tube with the outside are provided on both of the longitudinal tube (22) and horizontal tube(21). The tissue expander can be infused biological agents by the filling port to the skin expanding site through the small apertures (23), which may accelerate the expansion growth of skin, prevent skin complications, such as necrosis.

4 Claims, 1 Drawing Sheet

(56) References Cited

U.S. PATENT DOCUMENTS

| | | | | |
|---|---|---|---|---|
| 4,823,815 A * | 4/1989 | Watson | A61B 90/02 | 128/897 |
| 5,226,888 A * | 7/1993 | Arney | A61M 25/1002 | 604/103.07 |
| 5,336,178 A * | 8/1994 | Kaplan | A61B 8/12 | 604/103.01 |
| 5,484,411 A * | 1/1996 | Inderbitzen | A61M 25/1002 | 604/103.08 |
| 5,505,698 A * | 4/1996 | Booth | A61M 25/1002 | 604/103.11 |
| 5,522,790 A * | 6/1996 | Moll | A61B 17/0218 | 600/204 |
| 5,730,698 A * | 3/1998 | Fischell | A61F 2/86 | 600/3 |
| 5,772,680 A * | 6/1998 | Kieturakis | A61B 17/00234 | 600/207 |
| 5,810,767 A * | 9/1998 | Klein | A61B 8/12 | 604/103.01 |
| 5,865,728 A * | 2/1999 | Moll | A61B 17/0218 | 600/204 |
| 6,030,362 A * | 2/2000 | Boussignac | A61M 25/1002 | 604/101.01 |
| 6,478,807 B1 * | 11/2002 | Foreman | A61F 2/958 | 606/108 |
| 6,540,764 B1 * | 4/2003 | Kieturakis | A61B 17/00234 | 128/898 |
| 6,955,661 B1 * | 10/2005 | Herweck | A61L 29/041 | 604/103.01 |
| 7,004,963 B2 * | 2/2006 | Wang | A61F 2/958 | 606/192 |
| 8,100,855 B2 * | 1/2012 | Consigny | A61B 17/22 | 604/264 |
| 8,864,787 B2 * | 10/2014 | Muni | A61B 17/24 | 424/434 |
| 9,636,486 B2 * | 5/2017 | Consigny | A61M 25/104 | |
| 9,717,615 B2 * | 8/2017 | Grandt | A61F 2/958 | |
| 2003/0114793 A1 * | 6/2003 | Freyman | A61M 25/1002 | 604/103.1 |
| 2005/0075711 A1 * | 4/2005 | Neary | A61F 2/958 | 623/1.11 |
| 2008/0275569 A1 * | 11/2008 | Lesh | A61B 17/3468 | 623/23.72 |
| 2009/0198216 A1 * | 8/2009 | Muni | A61B 17/24 | 604/514 |
| 2010/0010470 A1 * | 1/2010 | Bates | A61L 29/126 | 604/509 |
| 2012/0283636 A1 * | 11/2012 | Rizq | A61M 25/10 | 604/103.02 |
| 2013/0150874 A1 * | 6/2013 | Kassab | A61B 17/32072 | 606/159 |
| 2015/0335859 A1 * | 11/2015 | Klocke | A61M 25/0108 | 623/1.11 |

* cited by examiner

SKIN DILATOR

This application is the U.S. national phase of International Application No. PCT/CN2014/073399 Filed on 13 March 2014 which designated the U.S. and claims priority to Chinese Application Nos. CN201310539646.2 filed on November 2013, the entire contents of each of which are hereby incorporated by reference.

FIELD OF THE INVENTION

The present invention relates to a medical device, and in particular, relates to a skin dilator that can provide additional biological effects.

BACKGROUND OF THE INVENTION

Currently the existing skin dilator is usually composed of an expander made of silicone material, an injection tube and an injection port. The injection tube is connected to the expander and the injection port. The expander is a sealed elastic bag that can be expanded several times. Two methods are adopted in use; one method is outside injection port method: to embed the expander to the subcutaneous tissue and the injection port and partial injection tube are outside of the body surface; and the other method is inside injection port method: to simultaneously embed the injection port and the injection tube to the subcutaneous tissue. By periodically injecting normal saline water through the injection port which reaches the subcutaneous expander via the injection tube, the expander is gradually expanding to dilate the skin, to form the expanded flap to repair the tissue defects on the body surface. The whole process takes 3-6 months.

At present, some complications may occur for the clinically used skin dilators during the treatment (about 20%-40% according to reports), such as local skin thinning, necrosis after the expansion of the embedded dilator after surgery, and sometimes even skin rupture in the expanding part, causing treatment failure and great losses to the patients and medical staffs.

SUMMARY OF THE INVENTION

The objective of the present invention is to solve the above problems, to provide a skin dilator which can provide additional biological effects simultaneously.

The objective of the present invention can be achieved through the following:

The present invention relates to a skin dilator that can provide additional biological effects, comprising the skin dilator body which is composed of an expander, a injection tube and a injection port, and the said injection tube is connected to the expander and injection port, wherein the said skin dilator further comprises a pipe network provided on the skin-side surface wall of the expander composed of longitudinal tube and horizontal tube having a reticular structure and communicating with each other, and a guide tube communicating the pipe network with a filling port, and several burrs distributed on the skin-side surface wall of the expander and located within the low-lying area of the grid formed by longitudinal tube and horizontal tubes, where several small apertures communicating the inner cavity of the pipe network with the outside are provided. The tissue expander can be infused biological agents by the filling port to the skin expanding site through the small apertures.

For the said skin dilator that can provide additional biological effects, wherein the said longitudinal tube is embedded in the skin-side surface wall of the expander and its top is flush with the skin-side surface wall, and the said horizontal tube is partially embedded within the skin-side surface wall of the said expander.

For the said skin dilator that can provide additional biological effects, one third to one half of the cross-section of horizontal tube protrude from the skin-side surface wall of the expander.

For the said skin dilator that can provide additional biological effects, the burrs within each grid formed by the said longitudinal tube and horizontal tube are distributed in plum blossom-shape or fence-shape, and the top of the said burrs is lower than the top of the said horizontal tube.

In the present invention, a pipe network provided on the skin-side surface wall of the expander composed of longitudinal tube and horizontal tube having a reticular structure and communicating with each other, and small apertures are provided on the surface of tubes, which communicate with a guide tube and a filling port (placed out of body and used to infuse biological agents). Thus, during the treatment with the skin dilator, cell suspension, cell growth factors or enriched stem cells can be infused through the guide tube, and expanded through the small apertures on the longitudinal tube and horizontal tubes, to reach the treatment sites such as inner surface of skin; and before the biological treatment, slightly reducing the tension of the expander by withdrawing some normal saline, through extrusion of the expanding skin, the friction between the skin and surface of dilator can be produced. Then the burrs on the skin-side surface of dilator may make some minor wounds in the inner surface of the skin, so that with the biological treatment (infusion of biological agents), the new repair and the growth of skin tissue will be greatly facilitated and accelerated, which improve the therapeutic effect and prevent complications through the action of biological agents.

DETAILED DESCRIPTION OF THE EMBODIMENTS

The invention is described herein in connection with drawings.

Figure 1:
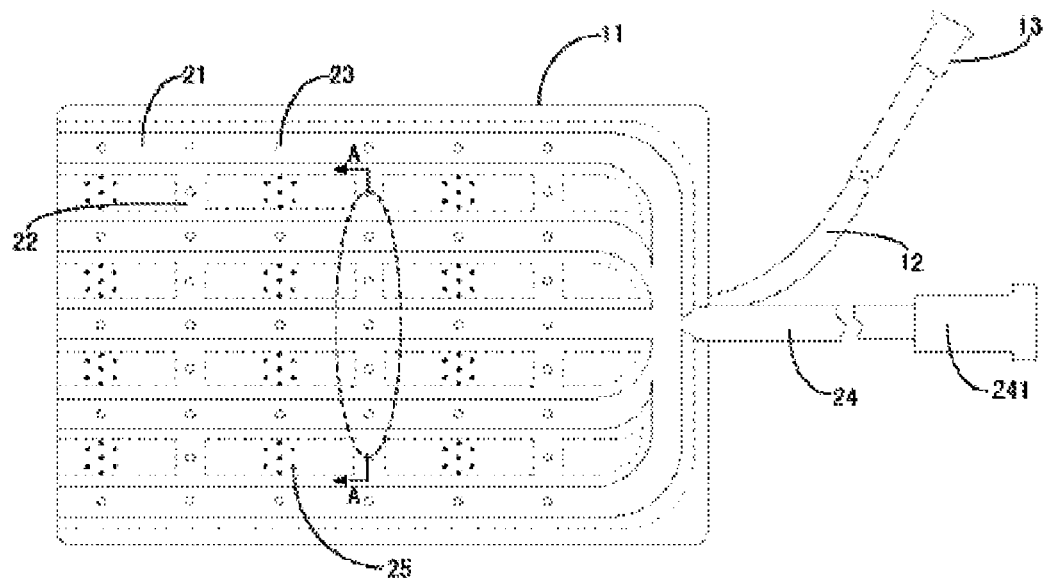
FIG. 1 is the schematic diagram of the invention.
Figure 2:
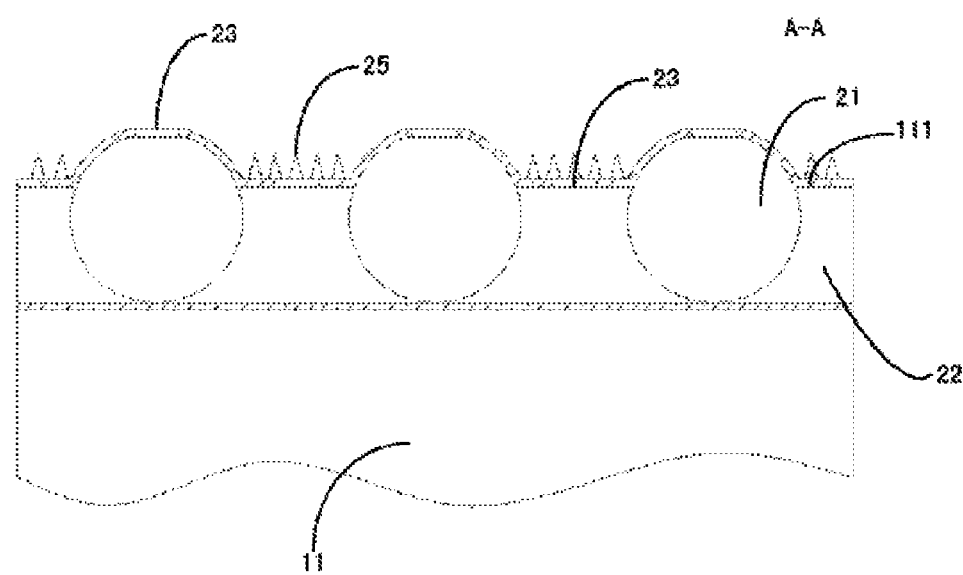
FIG. 2 is the partial cross-sectional view in the A-A direction in FIG. 1.

By referring to FIG. 1 and FIG. 2, the invention provides a skin dilator with additional biological effects, comprising the skin dilator body which is composed of an expander 11, an injection tube 12 and an injection port 13, and the said injection tube 12 is connected to the expander 11 and injection port 13 respectively, wherein the said skin dilator further comprises a pipe network provided on the skin-side surface wall 111 of the expander 11 (the skin-side surface wall 111 facing against the skin to be dilated) composed of longitudinal tube 22 and horizontal tube 21 having a reticular structure and communicating with each other, and a guide tube 24 communicating with the pipe network, and several burrs 25 distributed on the skin-side surface wall 111 of the expander 11 and located within the low-lying area of the grid formed by longitudinal tube 22 and horizontal tube 21. One end of the guide tube 24 is communicated with the longitudinal tube 22 at the end, and the other end is provided with the filling port 241. Small apertures 23 communicating the inner cavity with the outside are provided on the longitudinal tube 22 and horizontal tube 21. The diameter of small aperture 23 is 1-2 mm, less than the diameter of the cavity of the tube (longitudinal tube 22 and horizontal tube 21).

The said longitudinal tube 22 is embedded in the skin-side surface wall 111 of the expander 11 and its top is flush with the skin-side surface wall 111, and two thirds of the said horizontal tube 21 is embedded in the skin-side surface wall 111 of the expander 11 and one third of which protrudes from the skin-side surface wall 111 of the expander 11. The tubes are so elastic that they will not limit the expansion of the skin dilator.

The burrs 25 within each grid formed by the said longitudinal tube 22 and horizontal tube 21 are distributed in plum blossom-shape or fence-shape (not indicated in drawings), and the top of the said burrs 25 is lower than the top of the said horizontal tube 21.

During the treatment, the skin dilator is embedded in the subcutaneous tissue. Normal saline is injected to the expander 11 through the injection port 13 and injection tube 12. And in necessary, biological agents such as cell suspension, cell growth factors or enriched stem cells are injected by the filling port 241 and the guide tube 24. The cell suspension is infused through the small apertures 23 on the longitudinal tube 22 and horizontal tube 21, and is diffused to the subcutaneous tissue to be treated by the small apertures. Studies have shown that, stem cells can greatly enhance the therapeutic effect. In addition, due to a prolonged implantation of skin dilator, a layer of tissue membrane will be formed between the skin and the expander 11, which will hamper the biological agents access to the treatment site, affecting the therapeutic effect. Before the injection of biological agents, by the friction produced between the skin and the surface of the dilator, the tissue membrane will be damaged by the burrs on the surface of the dilator, forming some minor wounds by roughening the inner surface of skin. Thus, the stem cells, biological agents or drugs act on the treatment site of skin, which can greatly accelerate the growth of skin tissue, improve the therapeutic treatment and prevent complications.

The foregoing invention has been described in detail by way of illustration and example for purposes of clarity and understanding. As is readily apparent to one skilled in the art, the foregoing are only some of the methods and compositions that illustrate the embodiments of the foregoing invention. It will be apparent to those of ordinary skill in the art that variations, changes, modifications and alterations may be applied to the compositions and/or methods described herein without departing from the true spirit, concept and scope of the invention.

What is claimed is:

1. A skin dilator for providing additional biological effects, comprising a skin dilator body which is composed of an expander, an injection tube and an injection port, and the injection tube is connected to the expander and the injection port; wherein the skin dilator further comprises a pipe network provided on an outside of wall, which is closed to the skin of a subject, of the expander, the pipe network is composed of a longitudinal tube and a horizontal tube, which are connected, for forming a reticular structure, and a guide tube connected to the pipe network with a filling port, and several burrs distributed on the outside of the expander and located within the low-lying area of the reticular structure, where several small apertures communicating an inner cavity of the pipe network.

2. The skin dilator according to claim 1, wherein the longitudinal tube is embedded in an inside of wall, which is closed to the skin of the subject, of the expander and the end of the longitudinal tube is flush with the inside of wall, and the horizontal tube is partially embedded within the inside of wall of the expander.

3. The skin dilator according to claim 2, wherein one third to one half of cross-section of the horizontal tube protrudes from the outside of wall of the expander.

4. The skin dilator according to any one of claims 1-3, wherein the burrs within the reticular structure are distributed in plum blossom-shape or fence-shape, and the end of the burrs is lower than the end of the horizontal tube.

* * * * *